(12) United States Patent
Messina et al.

(10) Patent No.: US 7,731,391 B2
(45) Date of Patent: Jun. 8, 2010

(54) SYSTEM AND METHOD FOR PROVIDING A UNIFORM BACKLIGHT

(75) Inventors: Michael C. Messina, Hooksett, NH (US); Sheila Bergeron Dunn, Mason, NH (US)

(73) Assignee: Microscan Systems, Inc., Renton, WA (US)

( * ) Notice: Subject to any disclaimer, the term of this patent is extended or adjusted under 35 U.S.C. 154(b) by 0 days.

(21) Appl. No.: 11/758,774

(22) Filed: Jun. 6, 2007

(65) Prior Publication Data

US 2008/0080180 A1 Apr. 3, 2008

Related U.S. Application Data

(60) Provisional application No. 60/811,551, filed on Jun. 7, 2006.

(51) Int. Cl.
 *F21V 1/00* (2006.01)
 *F21V 11/00* (2006.01)
(52) U.S. Cl. .................. 362/235; 362/373; 362/332; 362/633; 362/224; 362/294; 362/612
(58) Field of Classification Search ............ 362/235, 362/311, 332, 633, 224, 225, 612, 294, 373
See application file for complete search history.

(56) References Cited

U.S. PATENT DOCUMENTS 5,416,683 A * 5/1995 McCarthy .................. 362/328

| | | | |
|---|---|---|---|
| 5,607,227 A | 3/1997 | Yasumoto et al. | |
| 5,936,353 A | 8/1999 | Triner et al. | |
| 2003/0174517 A1 | 9/2003 | Kiraly et al. | |
| 2005/0270766 A1* | 12/2005 | Kung et al. ............ | 362/97 |
| 2007/0103939 A1* | 5/2007 | Huang et al. ............ | 362/633 |

FOREIGN PATENT DOCUMENTS

DE 20 2004 009194 U1 12/2004

OTHER PUBLICATIONS 07109782.8-2423—European Search Report, Oct. 15, 2007, European Patent Office.

* cited by examiner

*Primary Examiner*—Sandra L O'Shea
*Assistant Examiner*—Jessica L McMillan
(74) *Attorney, Agent, or Firm*—Blakely Sokoloff Taylor & Zafman LLP

(57) ABSTRACT

An illumination system includes an illumination source such as an array of LED's over which is provided a diffuser. The illumination source provides light which, because of light refraction, radiates generally uniformly from edge to edge of the diffuser. The diffuser may be a planar flat piece of may include a hollow, cup like structure formed by a frame with a cover. The illumination system may be scaled up to provide multiple such illumination devices side by side to provide a greater area or strength of illumination. Multiple systems may utilize multiple diffusers or a single diffuser covering multiple illumination sources. The illumination source may be mounted to a backplate or heatsink which is larger than the illumination source to facilitate the addition of further electronic circuitry and or mounting capabilities.

13 Claims, 7 Drawing Sheets

SYSTEM AND METHOD FOR PROVIDING A UNIFORM BACKLIGHT

CROSS-REFERENCE TO RELATED APPLICATIONS

This application is related to and claims priority from U.S. provisional patent application No. 60/811,551 entitled Systems And Methods For Providing A Backlight filed Jun. 7, 2006 and fully incorporated herein by reference.

TECHNICAL FIELD

The present invention relates to illumination and lighting and more particularly, relates to a system and method for providing a illumination modules which can be scaled up in size and which provide uniform edge to edge illumination.

BACKGROUND INFORMATION

There are many uses for illumination systems. For example, it is necessary to use a source of illumination to provide automated product inspection. In such inspection systems, the inspection camera and software may be the same while the customer may want to change the product to be inspected. In one application, the product may be smaller than in another and accordingly, a smaller illumination source may work well for the smaller product while a larger illumination source will be required for the larger product.

In the past, a new illumination system had to be designed for each product to be inspected thus making it difficult for a customer to scale up or down in illumination system to work with an existing inspection system. Accordingly, there is a need for an illumination system which can be scaled up or down and which provides uniform and consistent illumination from edge to edge of the illumination system.

SUMMARY

The present invention features an illumination system providing generally uniform illumination from edge to edge. The illumination system comprises at least one illumination device including a source of illumination and a diffuser, disposed proximate the source of illumination and between the source of illumination and an object to be illuminated. The diffuser is made of a light transmissive material and includes a generally planar surface and is disposed a spaced distance from the source of illumination. The diffuser is configured for radiating light from the source of illumination through generally at least the entire planar surface of the diffuser by means of internal light refraction.

The source of illumination may be a single illumination element or multiple illumination element. The illumination elements may include LED elements. The LED elements are typically mounted together on one module or circuit board like structure.

In the preferred embodiment, the diffuser comprises a frame including a left side, right side, top side and bottom side, the frame having a height. The diffuser includes a generally planar cover extending between all the sides and having a length and a width. The cover disposed a spaced distance away from the source of illumination corresponding to the height of the frame. The sides and cover of the diffuser form a hollow cup like structure for radiating light from the source of illumination through generally at least the entire planar surface of the cover. The diffuser is typically the same size as the source of illumination.

The illumination system may include a plurality of the illumination devices mounted edge to edge to create a single larger illumination system of generally uniform illumination.

The source of illumination may include a back plate to which the source of illumination is mounted. The backplate has a width and a length which is generally the same as a length and width as the source of illumination. The backplate is typically larger than the source of illumination along at least one of the length and width of the backplate.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
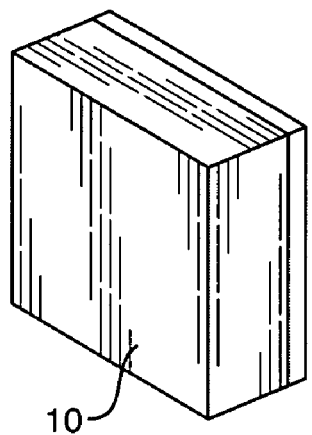
FIG. 1 is a schematic view of an illumination device in accordance with the present invention.
Figure 2:
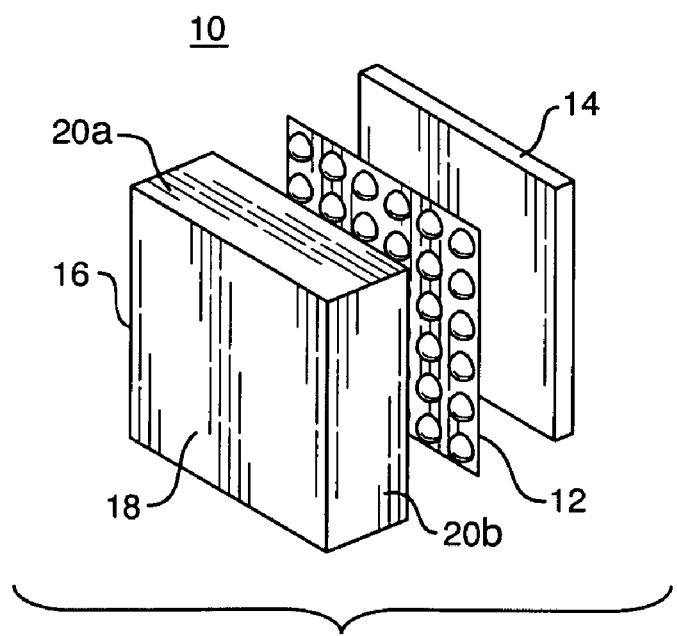
FIG. 2 is an exploded view of the illumination device of FIG. 1 in accordance with the present invention.

An illumination system 10, FIG. 1, in accordance with the present invention, includes an illumination source 12, FIG. 2, mounted to a mounting plate or heatsink 14 and over which is mounted a diffuser 16. In the preferred embodiment, the illumination source 12 includes a plurality of LEDs mounted on a printed circuit board. The LEDs may be of any color, combination of colors and/or strength required to illuminate an object of interest. The mounting plate or heatsink 14 serves to provide a generally rigid mounting area for the light source 12 and also provides for heat dissipation from the light source.

Figure 3:
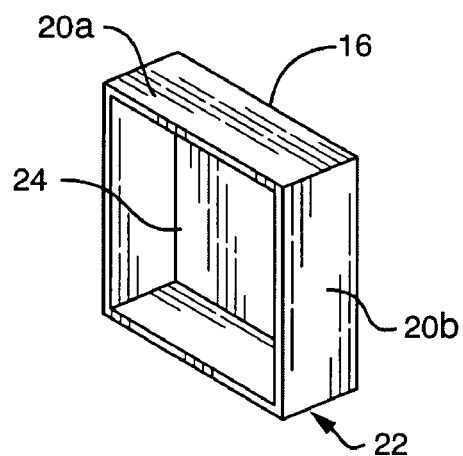
FIG. 3 is a schematic view of a diffuser in accordance with the teachings of the present invention without the cover in place.

In a first embodiment, diffuser 16 includes at least a flat piece of material 18 which is placed in front of the illumination source 12 and serves to defuse or spread the light evenly from each of the individual LEDs or other illumination device which makes up the illumination source 12. In the preferred embodiment, diffuser 16 includes a cover 18 and four sides 20. The sides 20 are arranged to form a frame 22, FIG. 3, defining a hollow central region 24 which fits over the light source 12. Although frame 22 is shown as a square frame, this is not a limitation of the present invention as any shape is contemplated. In the preferred embodiment, the shape of the diffuser frame 22 will generally correspond to the shape and size of the illumination source 12.

Diffuser 16 is made from a light transmissive material such as acrylic. In one embodiment, cover 18 snaps on or is otherwise fastened in place over the frame 22 to form a cup like structure which serves to generally uniformly provide illumination through the cover 18 from edge to edge of the diffuser 16 using internal refraction of the light within the diffuser.

Figure 4:
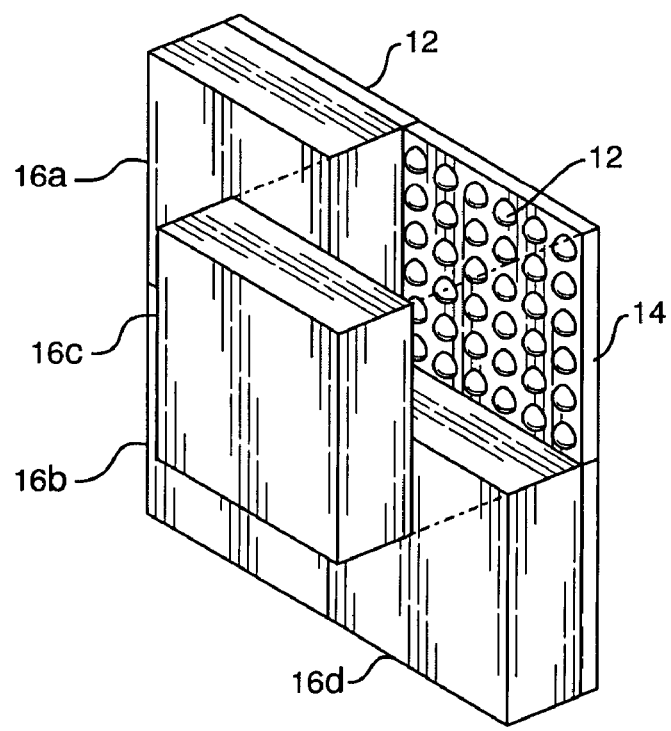
FIG. 4 is a partially assembled view of an illumination system having multiple illumination devices in accordance with the teachings of the present invention.
Figure 5:
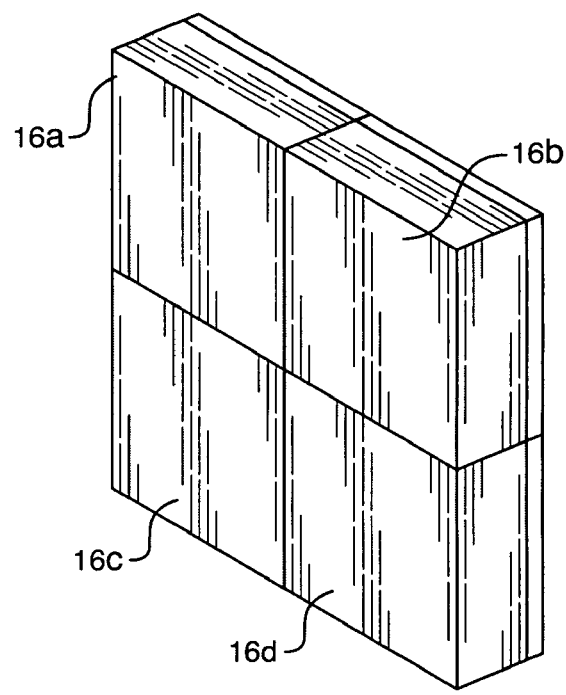
FIG. 5 is a schematic front view of the fully assembled illumination system of FIG. 4 having multiple illumination devices.
Figure 6:
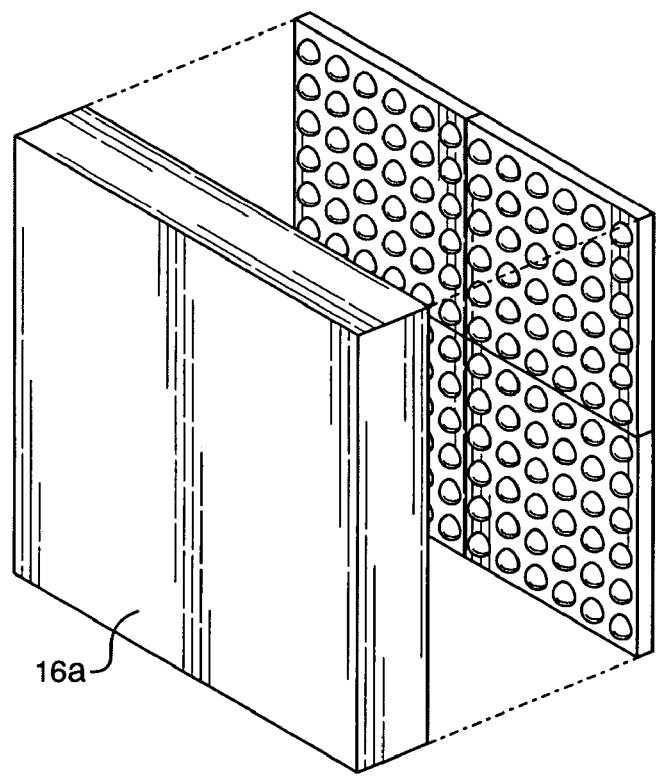
FIG. 6 is an exploded view of an illumination system having multiple illumination devices with one diffuser.
Figure 7:
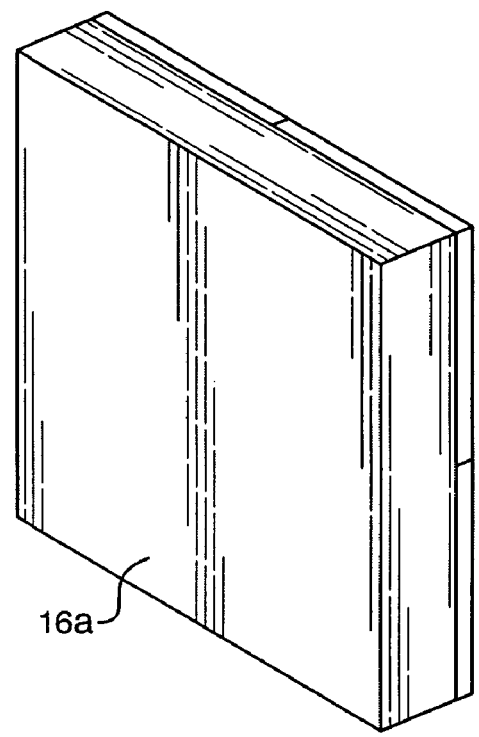
FIG. 7 is an assembled view of the illumination device of FIG. 6.

Although the illumination system of the present invention may be used as a single stand-alone illumination device, one feature the present invention is the ability to scale up the illumination system by providing a plurality of illumination devices 10, FIG. 4, as one illumination system. As shown, multiple illumination sources 12 and be placed on a backing plate 14 to form a larger and therefore more powerful light source. An additional feature of the present invention is the ability to substitute multiple diffusers 16, FIGS. 4 and 5 with a single larger diffuser 16a, FIGS. 6 and 7 which increases the uniformity of the light by eliminating seams between multiple diffusers.

Figure 8:
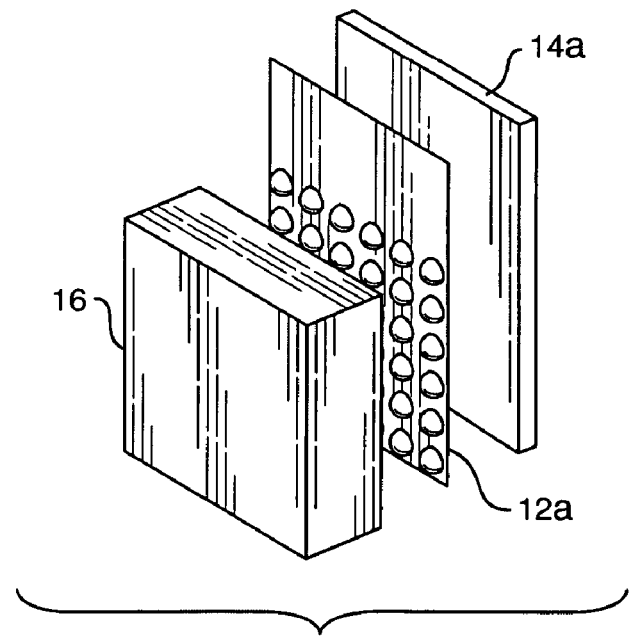
FIG. 8 is an exploded view of an illumination system having an illumination source mounted on a backing plate which is larger than the diffuser.
Figure 9:
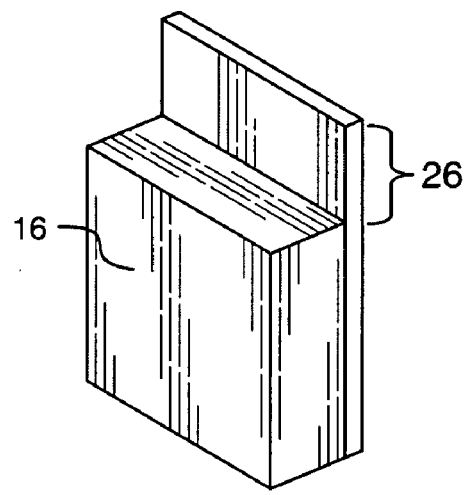
FIG. 9 is an assembled view of the illumination device of FIG. 8.
Figure 10:
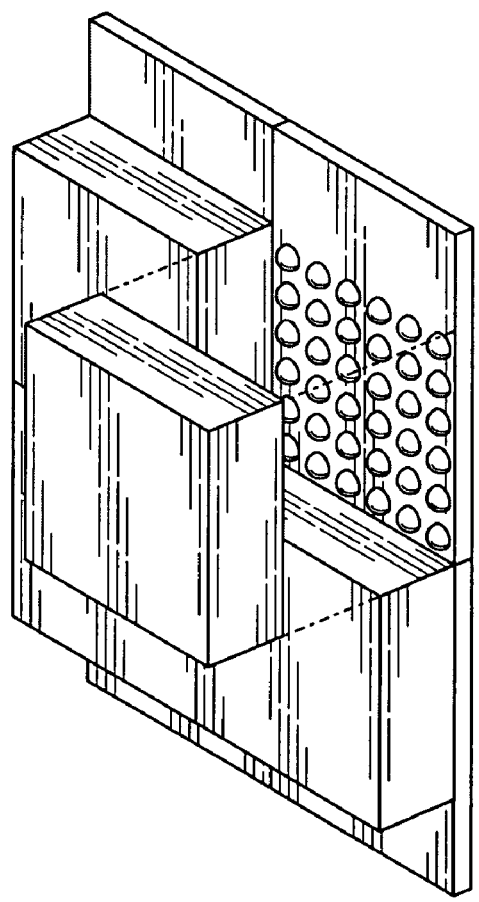
FIG. 10 is an exploded view of an illumination system having multiple illumination sources mounted on a backing plate which is larger than the size of multiple diffusers.
Figure 12:
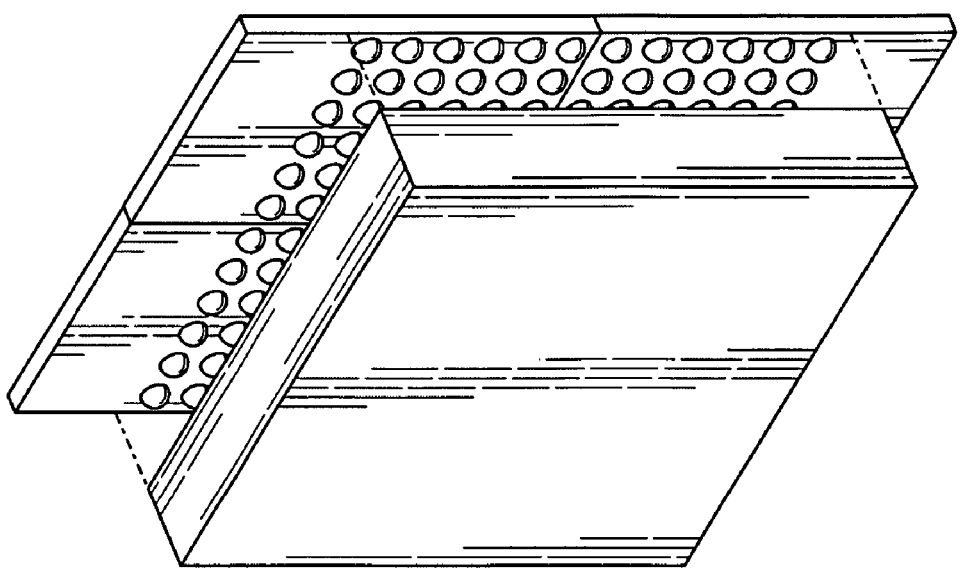
FIG. 12 is an exploded view of an illumination system having multiple illumination sources mounted on a backing plate which is larger than the size of a single diffuser.
Figure 11:
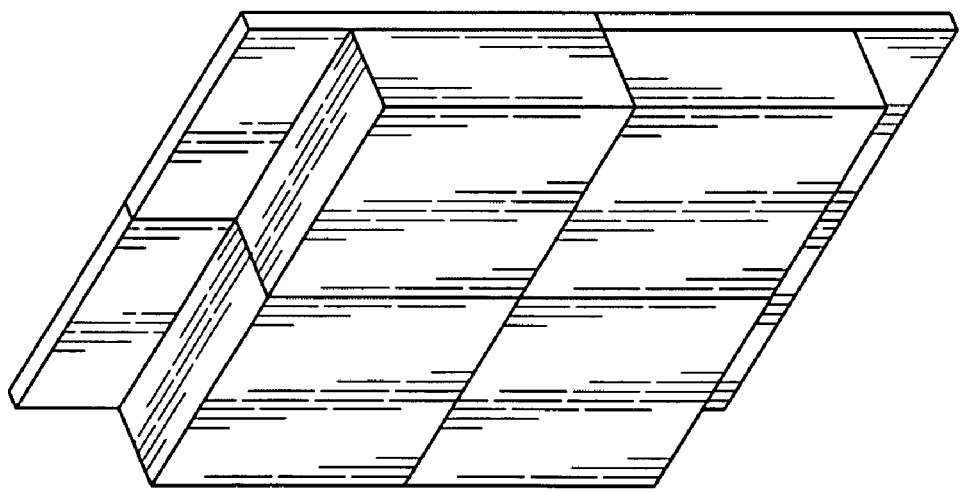
FIG. 11 is an assembled view of the illumination device of FIG. 10.
Figure 13:
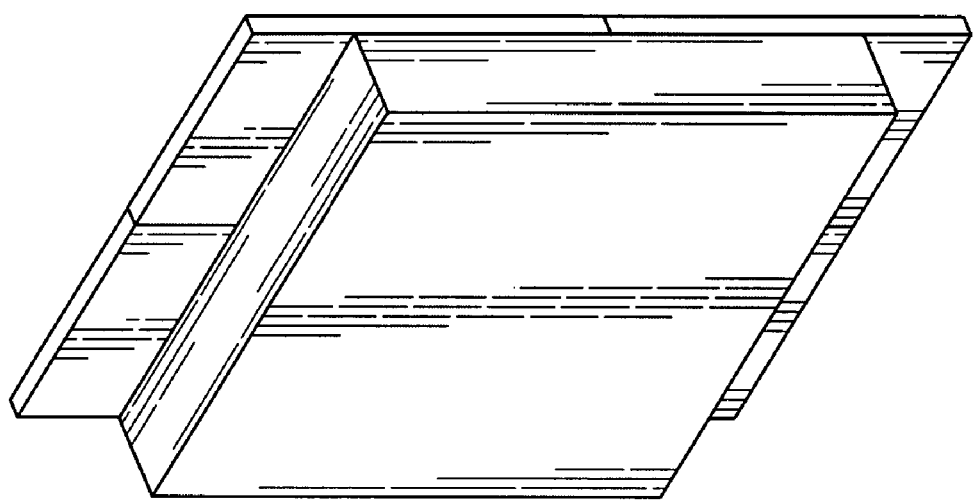
FIG. 13 is an assembled view of the illumination device of FIG. 12.

An additional feature of the present invention is the ability to provide an illumination source 12a and/or mounting plate 14a FIG. 8 with an extended region 26, FIG. 9 which extends beyond the length and width of the diffuser 16. Such an extended length allows for the mounting of additional electronic circuitry or for mounting the illumination system to an additional structure. This feature can also be used with multiple illumination sources and multiple diffusers FIGS. 10 and 11 as well as multiple illumination sources and a single diffuser FIGS. 12 and 13. In addition, as will be apparent to those skilled in the art, the extended region 26 may be provided on one or more sides of the illumination system.

Modifications and substitutions by one of ordinary skill in the art are considered to be within the scope of the present invention, which is not to be limited except by the following claims.

The invention claimed is:

1. A modular illumination system comprising:
   two or more illumination modules, each illumination module comprising:
      a heat sink,
      a substrate coupled to the heat sink, the substrate having one or more light sources mounted thereon, and
      a diffuser comprising a frame having a proximal end and a distal end, and a front cover attached to the distal end, wherein the proximal end of the frame is removably attached to the substrate; and
   wherein the two or more illumination modules are coupled to each other along their respective edges such that the diffuser of each module abuts the diffuser of at least one adjacent module.

2. The modular illumination system of claim 1 wherein a hollow volume is formed between each substrate and its corresponding diffuser such that the one or more light sources are enclosed within the hollow volume.

3. The modular illumination system of claim 1 wherein the length and width of each frame substantially corresponds to the length and width of its corresponding substrate.

4. The modular illumination system of claim 1 wherein on at least one of the illumination modules one or both of the length and width of the substrate exceeds the corresponding length or width of the frame.

5. The modular illumination system of claim 1 wherein the diffusers of all illumination modules are removed and replaced with a single diffuser that diffuses light from all illumination modules.

6. The modular illumination system of claim 5 wherein the single diffuser is removably attached around the perimeter of the coupled illumination modules.

7. A modular illumination system comprising:
   two or more illumination modules, each illumination module comprising:
      a substrate having one or more light sources mounted thereon, and
      a diffuser comprising a frame having a proximal end and a distal end, and a front cover attached to the distal end, wherein the proximal end of the frame is removably attached to the substrate; and
   wherein the two or more illumination modules are coupled to each other along their respective edges such that the diffuser of each module abuts the diffuser of at least one adjacent module.

8. The modular illumination system of claim 7 wherein a hollow volume is formed between each substrate and its corresponding diffuser such that the one or more light sources are enclosed within the hollow volume.

9. The modular illumination system of claim 7 wherein the length and width of each frame substantially corresponds to the length and width of its corresponding substrate.

10. The modular illumination system of claim 7 wherein on at least one of the illumination modules one or both of the length and width of the substrate exceeds the corresponding length or width of the frame.

11. The modular illumination system of claim 7 wherein each illumination module further comprises a heat sink attached to the substrate.

12. The modular illumination system of claim 7 wherein the diffusers of all illumination modules are removed and replaced with a single diffuser that diffuses light from all illumination modules.

13. The modular illumination system of claim 12 wherein the single diffuser is removably attached around the perimeter of the coupled illumination modules.

* * * * *